United States Patent [19] [11] 4,153,564
Chibnik [45] May 8, 1979

[54] NITROGEN-CONTAINING COMPOUNDS AND LUBRICANT COMPOSITIONS CONTAINING SAME

[75] Inventor: Sheldon Chibnik, Cherry Hill, N.J.

[73] Assignee: Mobil Oil Corporation, New York, N.Y.

[21] Appl. No.: 899,678

[22] Filed: Apr. 24, 1978

[51] Int. Cl.$^2$ .................. C10H 1/22; C07D 207/12; C07D 249/18
[52] U.S. Cl. ................... 252/51.5 A; 44/63; 260/326.5 F; 260/308 B
[58] Field of Search .................. 44/63, 71, 73; 260/326.5 F, 308 B, 570.5; 544/94; 252/357, 403, 542, 51.5 A

[56] References Cited

U.S. PATENT DOCUMENTS

| | | | |
|---|---|---|---|
| 3,235,497 | 2/1966 | Lee | 44/71 |
| 3,346,493 | 10/1967 | Suer | 252/32.5 |
| 3,380,909 | 4/1968 | Lee | 252/403 |
| 3,413,104 | 11/1968 | Mehmedbasich | 44/63 |
| 3,497,334 | 2/1970 | Gee et al. | 44/63 |
| 3,507,880 | 4/1970 | Altwicker | 44/71 |
| 3,649,229 | 3/1972 | Otto | 44/73 |
| 3,948,619 | 4/1976 | Worrel | 44/53 |
| 4,006,089 | 2/1977 | Chibnik | 252/51.5 |

*Primary Examiner*—Allen B. Curtis
*Assistant Examiner*—Raymond Covington
*Attorney, Agent, or Firm*—Charles A. Huggett; Raymond W. Barclay; Claude E. Setliff

[57] ABSTRACT

Compounds that act as emulsifiers, detergents and antioxidants when added to a lubricant or a fuel are prepared from (1) an alkenylsuccinic anhydride or acid and an aniline-aldehyde resin or (2) the product of (1) and an aromatic triazole, e.g. benzotriazole, and aldehyde. Also included are lubricant compositions containing the compounds.

18 Claims, No Drawings

NITROGEN-CONTAINING COMPOUNDS AND LUBRICANT COMPOSITIONS CONTAINING SAME

BACKGROUND OF THE INVENTION

Field of the Invention

The invention relates to lubricant and fuel additives. It is especially concerned with a class of products made by reaction of an alkenylsuccinic anhydride with arylamine-aldehyde moieties.

Discussion of the Prior Art

A great deal of effort is being directed to providing a lubricant which will permit present-day automotive engines to be operated at high level of efficiency over long periods of time. A difficulty arises because lubricating oils tend to deteriorate under the conditions of use, with attendant formation of sludge, lacquer and resinous materials which adhere to the engine parts, thereby lowering the operating efficiency of the engine. To counteract the formation of these deposits, certain chemical additives have been found which, when added to lubricating oils, have the ability to keep the deposit-forming materials suspended in the oil, so that the engine is kept clean and in efficient operating condition for extended periods of time. These added agents are known in the art as detergents or dispersants.

Certain Mannich Base-type additives are known in the art to be effective lubricant and fuel additives, especially as detergents. U.S. Pat. No. 3,649,229, for example, discloses Mannich products made using high molecular weight hydroxyaromatic compounds, as does U.S. Pat. No. 3,948,619. The former patent teaches the reaction of an alkenylsuccinic anhydride or acid with an amine. U.S. Pat. No. 4,006,089 also discloses a Mannich product made using a high molecular weight hydroxyaromatic compound. It discloses the use of an unconventional amine as the nitrogen compound.

The reaction of amines, as for example, aniline, with an aldehyde, e.g. formaldehyde, to form a resin is known, as is the formation of amides with compounds containing the anhydride function. Obviously, the Mannich reaction is known to the art. However, no art is known that teaches or suggests the compounds of this invention or lubricant or fuel compositions containing them.

SUMMARY OF THE INVENTION

In accordance with the invention there is provided a product made by reacting an alkenylsuccinic anhydride with a resin prepared from an aromatic amine and an aldehyde. Also, it provides a product made by reacting alkenylsuccinic anhydride with an amine-aldehyde resin, triazole and aldehyde. As an example the product may be made by (1) reacting an alkenylsuccinic anhydride with a resin prepared from an aromatic amine and an aldehyde and (2) reacting the material from (1) with an aromatic triazole and an aldehyde. The invention further provides a lubricant composition containing either of the said products.

DESCRIPTION OF SPECIFIC EMBODIMENTS

In general aspect, the invention pertains to two classes of compounds, each novel, and their use in lubricants or fuels. The first of these can be made by a scheme summarized by the following:

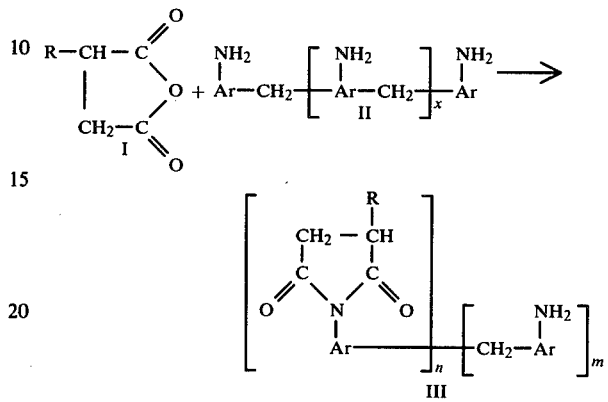

where Ar is an aromatic hydrocarbyl containing 6 to 18 carbon atoms, specifically derived, for example, from benzene, naphthalene and anthracene, R is an alkenyl group containing from 40 to 1000 carbon atoms, preferably having 50 to 250 carbon atoms, n is from 1 to 3, x is from 0 to 4, preferably 0 to 2 and m is from 1 to 3.

The succinic anhydride used is prepared by conventional means. The alkenylsuccinic member is obtained by reaction of the anhydride with a polymer made from an olefin such as ethylene, propylene or butene or with a copolymer of these.

Another of the reactants, the aromatic amine-aldehyde product may be purchased. For instance, a resin said by Jefferson Chemical Company to have the formula set forth in Example 1 is available. They can be prepared generally by reacting, at from about 60° to 120° C., an aromatic amine and an aldehyde in a ratio to yield the product II as set forth above.

While the use of aniline is preferred, other aromatic amines can be used. In general they will include those having from 6 to 18 carbon atoms, which may include substituent groups, preferably alkyl. The aldehydes useful in the reaction include the preferred formaldehydes. Also included are paraformaldehyde, acetaldehyde and furfural.

The reaction of the alkenylsuccinic anhydride with the amine-aldehyde resin is carried out at from about 50° C. to about 250° C., preferably about 100° C. to about 150° C. Times will vary, depending upon many factors, but will generally range from about 30 minutes to about 6 hours, preferably about 1 to about 3 hours. Solvents may be used if desired. The hydrocarbon solvents in which the reactants and products are soluble, or from which they are easily removed are preferred.

The product thus obtained, although itself effective in the utilities specified above, can be further reacted with an aromatic triazole and aldehyde. The following illustrates the product using benzotriazole and formaldehyde:

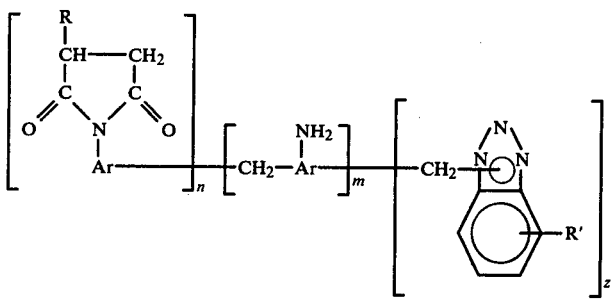

wherein R is as defined hereinabove, R' is hydrogen or a lower alkyl group, i.e. one containing 1–6 carbon atoms, n an m are as above defined and z is 1 to 2.

Broadly, this reaction is carried out by mixing the aldehyde and aromatic triazole with the initial reaction product (anhydride-amine-aldehyde product). In general, the aldehyde: triazole mole ratio will be 1:1, but the excess aldehyde may be present up to 30%. The temperature of the reaction will be from about 50° C. to about 175° C., preferably about 85° C. to about 110° C. After the reaction is completed, the volatiles are removed, generally at 150° to 175° C. Times of reaction will vary depending upon the reactants chosen, but will generally range from about 0.5 to about 5 hours, preferably from about 1 to about 3 hours. As mentioned in the description of the process for making the initial product, solvents may be used in carrying out this reaction.

The fuels in which the compounds of the invention may be used include the mixtures of hydrocarbons boiling in the gasoline range, usually from about 100° to 425° F. They can consist of straight or branched-chain paraffins, cycloparaffins, olefins and aromatic compounds or any mixture of such compounds. The gasolines can contain other additives such as anti-knock compounds and the like as well as scavenging agents, dyes and antiicing agents. Normally, the gasoline will contain from about 0.002% to about 0.05% by weight of the reaction product of alkenylsuccinic anhydride with the amine-aldehyde resin, preferably about 0.01 to 0.04% by weight. It will contain about 0.002% to about 0.05% by weight, preferably about 0.01% to 0.04% by weight of the product of reaction between the just mentioned product and an aldehyde and an aromatic triazole. Functionally the fuels, as well as the lubricants, will contain an amount sufficient to improve the emulsifying, antioxidant and detergent properties thereof.

The lubricants which may be used with the products of this invention are mineral and synthetic lubricating oils and greases therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethylhexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof, (2) 2,2-disubstituted propane diols and (3) the pentaerythritols reacted with aliphatic monocarboxylic acids containing from about 4 to 9 carbon atoms. Mixtures of these acids may be used to prepare the esters.

Preferred among the esters are those made from pentaerythritol and a mixture of $C_5$–$C_9$ acids.

The lubricant will contain, on a % by weight basis, from about 0.1% to about 10%, preferably about 1% to 6%, of the alkenylsuccinic anhydride-resin product or from about 0.1% to about 10%, preferably about 1% to 6% of the reaction product of the just mentioned product with aldehyde and triazole.

The following will serve to illustrate the invention:

EXAMPLE 1

Forty-one parts of a mixture of products said by the manufacturer to have the formula

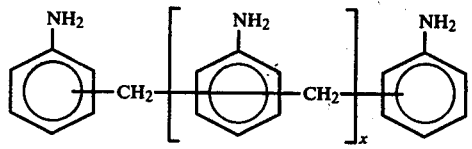

where x is either 0, 1 or 2, was reacted with 412 parts of polyisobutenylsuccinic anhydride (prepared using 1300 molecular weight polyisobutene) at 150° C. for 3 hours under a 5 mm vacuum. The product was diluted with a light mineral oil and was filtered.

EXAMPLE 2

Twelve parts of the reactant shown in Example 1 and 130 parts of the same polyisobutenylsuccinic anhydride were reacted for 3 hours at 150° C. under a 2 mm vacuum. The molar ratio of anhydride to resin was 1:1. The product was diluted with 150 parts of light oil and was cooled to 95° C. Eight parts of tolyltriazole was added and a total of 3 parts of paraformaldehyde was added in equal portions over a 1-hour period. The reaction was completed by removal of volatiles at 150° C. for 1 hour at 2 mm of pressure.

EXAMPLE 3

Polyisobutenyl (500 m. wt.) succinic anhydride (100 parts) and 31 parts of the resin shown in Example 1 were reacted, and this product was reacted with 19 parts of benzotriazole and 6.3 parts of paraformaldehyde. Reaction conditions were similar to those of Examples 1 and 2.

EXAMPLE 4

Under conditions similar to those outlined in Examples 1 and 2, a product was made using 130 parts of polyisobutenyl (1300) succinic anhydride, 15 parts of the Example 1 amine-aldehyde resin, 8 parts of tolyltriazole and 3 parts of paraformaldehyde.

EVALUATION OF PRODUCTS

Test for Emulsification

The products described above were examined for emulsibility by dissolving 1.3% of each in a 100" solvent refined, paraffinic, neutral oil and testing in accordance with ASTM D-1401. In general, equal volumes of oil plus additive and water are stirred for 5 minutes at 130° F. in a graduated cyclinder. The time required for the separation of the emulsion thus formed is recorded. If separation does not occur after standing one hour, the volumes of oil, water and emulsion remaining at that time are reported. There was no separation of oil or water with either of the Example 1 and 2 products.

Diesel Oil Test 3.2 parts of the respective products (on an oil-free basis) was compounded with 1.6 parts of calcium sulfonate, 0.4 part of calcium phenate and 1 part of zinc alkyldithiophosphate in 98.3 parts of solvent refined SAE30 grade lubricating oil. The base fluid and the same base fluid containing the aforementioned individual additives were next subjected for evaluation in a diesel oil test. This test was developed to produce deposits from the oxidation of lubricating oil under conditions which closely approximate those found in the piston zone of a diesel engine. The test consists of an aluminum cylinder heated by radiant energy from an internal heater. The surface temperature of the heater is maintained at 575° F. during the test period (140 minutes). The shaft turns slowly (2 RPM) and into an oil sump where it picks up a thin film of oil. This thin film is carried into the oxidation zone where heated gases (moist air at 350° F. is typically employed, however, nitrogen oxides, sulfur oxides and other mixtures can be used) to form oxidation deposits. These deposits can be affected by the detergent as the test cylinder rotates into the sump. The efficiency of the detergent is rated by the color and intensity of the deposit on the shaft at the end of the test. The comparative results obtained employing this test, are shown in the table below.

Antioxidant Test

In this test, the additive is placed in an oil, and then the composite is heated to 375° C. Dry air is passed through it at the rate of 10 pounds per hour. There are also present in the composite iron, copper, aluminum and lead. After 24 hours the neutralization number (NN) for each oil composition is obtained according to ASTM Method D741-1. The effectiveness of the additive is revealed by comparison of the control of viscosity increase ($\Delta KV$) and control of acids ($\Delta NN$) with the additive-free oil or standard.

TABLE

| Diesel Oil Test (100 = Clean) | Ex. 1 | Ex. 2 | Standard* |
|---|---|---|---|
| 140 min. | 74.0 | 68.0 | 50 |
| Antioxidant Test 375° C., 24 hrs. | | | |
| Viscosity, 100° F., cs | 175.2 | 32.3 | 323.8 |
| Sludge | Trace | Trace | Heavy |

*Solvent refined SEA 30 Mineral Oil

I claim:

1. A product having the following formula $$\left[ \begin{array}{c} R-CH-C\overset{O}{\underset{\|}{\parallel}} \\ | \\ CH_2-C \\ \underset{\|}{\parallel} \\ O \end{array} \diagup N-Ar \right]_n \left[ -CH_2-Ar \overset{NH_2}{\underset{|}{}} \right]_m$$

wherein R is an alkenyl group containing from 40 to 1000 carbon atoms, Ar is an aromatic hydrocarbyl containing 6 to 18 carbon atoms, n is from 1 to 3 and m is from 1 to 3.

2. The product of claim 1 wherein the alkenyl group has a number average molecular weight of 1300.

3. The product of claim 1 wherein the alkenyl group has a number average molecular weight of 500.

4. A composition comprising a lubricant or liquid hydrocarbon fuel and from about 0.1 percent to about 10 percent by weight of the product of claim 1.

5. A composition comprising a lubricant or liquid hydrocarbon fuel and from about 0.1 percent to about 10 percent by weight of the product of claim 2.

6. A composition comprising a lubricant or liquid hydrocarbon fuel and from about 0.1 percent to about 10 percent by weight of the product of claim 3.

7. A product having the following formula $$\left[ \begin{array}{c} R-CH-C\overset{O}{\underset{\|}{\parallel}} \\ | \\ CH_2-C \\ \underset{\|}{\parallel} \\ O \end{array} \diagup N-Ar \right]_n \left[ -CH_2-Ar \overset{NH_2}{\underset{|}{}} \right]_m$$

$$\left[ -CH_2-N \diagdown \begin{array}{c} N \\ \diagup \\ \diagdown \\ N \end{array} -R' \right]_z$$

wherein R is an alkenyl group containing 40 to 1000 carbon atoms, R' is hydrogen or a lower alkyl, Ar is an aromatic hydrocarbyl containing 6 to 18 carbon atoms, n is from 1 to 3, m is from 1 to 3 and z is from 1 to 2.

8. The product of claim 7 wherein the alkenyl group has a number average molecular weight of 1300.

9. The product of claim 7 wherein the alkenyl group has a number average molecular weight of 500.

10. The product of claim 7 wherein R' is $C_1$-$C_6$ alkyl.

11. The product of claim 10 wherein R is methyl.

12. The product of claim 7 wherein R is hydrogen.

13. A composition comprising a lubricant or liquid hydrocarbon fuel and from about 0.1 percent to about 10 percent by weight of the product of claim 7.

14. A composition comprising a lubricant or liquid hydrocarbon fuel and from about 0.1 percent to about 10 percent by weight of the product of claim 8.

15. A composition comprising a lubricant or liquid hydrocarbon fuel and from about 0.1 percent to about 10 percent by weight of the product of claim 9.

16. A composition comprising a lubricant or liquid hydrocarbon fuel and from about 0.1 percent to about 10 percent by weight of the product of claim 10.

17. A composition comprising a lubricant or liquid hydrocarbon fuel and from about 0.1 percent to about 10 percent by weight of the product of claim 11.

18. A composition comprising a lubricant or liquid hydrocarbon fuel and from about 0.1 percent to about 10 percent by weight of the product of claim 12.

* * * * *